(12) United States Patent
Mandel

(10) Patent No.: US 11,534,413 B2
(45) Date of Patent: *Dec. 27, 2022

(54) CANNABINOID POUCHES

(71) Applicant: TRINIDAD CONSULTING, LLC, Arcata, CA (US)

(72) Inventor: Case Mandel, Arcata, CA (US)

(73) Assignee: Trinidad Consulting, LLC, Arcata, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/579,579

(22) Filed: Jan. 19, 2022

(65) Prior Publication Data
US 2022/0142942 A1 May 12, 2022

Related U.S. Application Data

(63) Continuation of application No. 17/315,066, filed on May 7, 2021.
(Continued)

(51) Int. Cl.
| | |
|---|---|
| *A61K 31/05* | (2006.01) |
| *A61K 9/00* | (2006.01) |
| *A61K 35/36* | (2015.01) |
| *A61K 36/258* | (2006.01) |
| *A61K 31/375* | (2006.01) |
| *A61K 31/4045* | (2006.01) |
| *A61K 36/185* | (2006.01) |

(Continued)

(52) U.S. Cl.
CPC ............. *A61K 31/05* (2013.01); *A61K 9/009* (2013.01); *A61K 9/0056* (2013.01); *A61K 9/70* (2013.01); *A61K 31/015* (2013.01); *A61K 31/045* (2013.01); *A61K 31/197* (2013.01); *A61K 31/352* (2013.01); *A61K 31/375* (2013.01); *A61K 31/4045* (2013.01); *A61K 31/522* (2013.01); *A61K 31/575* (2013.01); *A61K 31/675* (2013.01); *A61K 31/706* (2013.01); *A61K 35/36* (2013.01); *A61K 36/185* (2013.01); *A61K 36/258* (2013.01); *A61K 36/53* (2013.01); *A61K 47/46* (2013.01)

(58) Field of Classification Search
CPC .... A61K 36/258; A61K 31/522; A61K 9/009; A61K 36/185; A61K 31/675; A61K 31/352; A61K 31/575; A61K 31/05; A61K 9/0056; A61K 31/015; A61K 31/197; A61K 31/375; A61K 31/4045; A61K 9/70; A61K 47/44; A61K 31/706; A61K 9/006; A61K 35/36; A61K 36/53; A61K 31/045; A61K 47/46; A61M 35/00
See application file for complete search history.

(56) References Cited

U.S. PATENT DOCUMENTS

| | | |
|---|---|---|
| 9,265,272 B2 | 2/2016 | Gedevani et al. |
| 9,913,491 B2 | 3/2018 | Rushforth et al. |

(Continued)

FOREIGN PATENT DOCUMENTS

| | | | |
|---|---|---|---|
| WO | WO-2014089649 A1 * | 6/2014 | ......... A61K 31/4425 |
| WO | 2018233781 A1 | 12/2018 | |
| WO | 2019211771 A1 | 11/2019 | |

*Primary Examiner* — Jianfeng Song
(74) *Attorney, Agent, or Firm* — Rimon PC

(57) ABSTRACT

The present invention relates to apertured pouches comprising a fibrous matrix containing a cannabinoid and/or terpene ingredient, including kits, methods of use and methods of manufacture.

15 Claims, 4 Drawing Sheets

Related U.S. Application Data

(60) Provisional application No. 63/021,661, filed on May 7, 2020.

(51) Int. Cl.
*A61K 31/706* (2006.01)
*A61K 31/522* (2006.01)
*A61K 31/675* (2006.01)
*A61K 31/197* (2006.01)
*A61K 36/53* (2006.01)
*A61K 47/46* (2006.01)
*A61K 9/70* (2006.01)
*A61K 31/352* (2006.01)
*A61K 31/015* (2006.01)
*A61K 31/045* (2006.01)
*A61K 31/575* (2006.01)

(56) References Cited

U.S. PATENT DOCUMENTS

| | | | |
|---|---|---|---|
| 2008/0302682 A1* | 12/2008 | Engstrom | A24B 13/00 206/260 |
| 2014/0287068 A1* | 9/2014 | Lewis | A01G 22/67 800/298 |
| 2018/0125777 A1* | 5/2018 | Lindsay | B65B 11/48 |
| 2018/0177720 A1 | 6/2018 | Cooper | |
| 2019/0060225 A1* | 2/2019 | Mandel | A61K 31/352 |
| 2019/0328678 A1 | 10/2019 | Sunderland | |
| 2021/0023046 A1* | 1/2021 | Bruun | A61K 47/12 |

* cited by examiner

CANNABINOID POUCHES

CROSS-REFERENCE TO RELATED APPLICATIONS

This application is a Continuation application of U.S. patent application Ser. No. 17/315,066, filed May 7, 2021, which claims priority to U.S. Provisional Patent Application No. 63/021,661, filed May 7, 2020. The contents of these applications are incorporated herein by reference in their entirety.

BACKGROUND

Many *Cannabis* smokers desire smokeless alternatives because of the cumulative adverse effects of smoking. Until recently the main alternative to smoked *Cannabis* was edible *Cannabis*. However, most users of edible *Cannabis* find that it has undesirable characteristics including slow action, often requiring an hour or more before effects are felt, and unpredictable dosing. Ingested cannabinoids are subject to first pass metabolism by the liver which generates metabolites with elevated psychoactivity. These problems are often exacerbated by users who subsequently consume additional quantities in the mistaken belief that their initial dose was inadequate. Negative health consequences may result from this dose disparity. This dose disparity is apparent and becoming better documented in a variety of other active ingredients consumed as nutraceuticals without the doctor prescription dosing or recommendations.

The recent proliferation of *Cannabis* concentrates has enabled a new generation of orally administered *Cannabis* products which allow for fast action and more consistent absorption. Concentrates produced by these extraction processes can be easily combined with edible ingredients for consistent dosing. Unfortunately, the resulting compositions continue to be slow acting because of the low water solubility of cannabinoids. Cannabinoids and the closely related terpenoids consist of combinations of five carbon isoprene units which have strong lipid character and are therefore not readily absorbed into blood until after being digested in the stomach.

Though the reasoning for it is unclear, conventional pouches for oral administration provide a slow and uneven oral release profile when incorporating *Cannabis* compositions. Therefore, there is a need in the art for a delivery mechanism that orally delivers *Cannabis* compositions in an even release profile.

The present invention addresses this and other related needs in the art.

SUMMARY

A pouch for administration of a cannabinoid is provided in frequent embodiments, which pouch comprises a fibrous matrix material incorporating a plurality of apertures defining a sealed pouch, and a cannabinoid and/or terpene containing fill material positioned within the sealed pouch. Often, the pouch further comprises a terpene in the cannabinoid containing fill material. Also often the fill material is comprised of coconut coir, kenaf, abaca, flax, hemp, jute, ramie, sisal, rice, bamboo, corn husk, silk husk, fruit skin, straw, soy, mint leaf, spearmint leaf, lettuce leaf, synthetic fibers, animal-derived fibers, chitin, kudzu root, or a combination of two or more of the foregoing. The apertures may be of uniform or varying sizes, with a diameter ranging often between at or about 200 μm to about at or about 1000 μm. Often the aperture density in such an embodiment is 1, 5, 10, 15, 20, 25, 30, 35, 40, 45, 50, 55, 60, 65, 70, 75, 80, 85, 90, 95, or 100. Also often about 60%, 65%, 70%, 75%, 80%, 85%, 90%, 95%, or 100% of the fill material particles are larger than the aperture size in the pouch or fibrous matrix material. Often in such embodiments the pouch is adapted to release between 40% to 90% of the cannabinoid present in the fill material in between 5 to 10 minutes, 4 to 15 minutes, 3 to 12 minutes, 4 to 10 minutes, or under 10 minutes after being placed in a mouth of a user.

Methods of administering a cannabinoid are also contemplated herein. According to an exemplary method a pouch comprised of a fibrous matrix material incorporating a plurality of apertures defining a sealed pouch, and a cannabinoid containing fill material positioned within the sealed pouch is introduced to the mouth of a subject and contacted with an oromucosal surface of the mouth of the subject. The pouch is thereafter maintained in the mouth of the subject between 1 minute to 30 minutes. In certain related embodiments, the pouch comprises a fibrous matrix material having a plurality of apertures on one or two opposing surfaces. Often the pouch comprises a fibrous matrix material having a plurality of apertures on (one of) a front or rear surface and the surface having the apertures is applied to the oromucosal surface of the mouth of the subject.

In often included embodiments, each of the plurality of apertures is defined by an aperture size of between about at or 200 μm or 300 μm to about at or about 800 μm in diameter. Also often, each of the plurality of apertures is defined by an aperture size of above at or about 200 μm or 300 μm or at or about 400 μm in diameter. In certain frequent embodiments, each of the plurality of apertures is defined by an aperture size of between at or about 200 μm or 300 μm to at or about 500 μm in diameter. In certain frequent embodiments, each of the plurality of apertures is defined by an aperture size of between at or about 200 μm or 300 μm to at or about 600 μm in diameter. In certain frequent embodiments, each of the plurality of apertures is defined by an aperture size of between at or about 200 μm or 300 μm to at or about 700 μm in diameter. In certain frequent embodiments, each of the plurality of apertures is defined by an aperture size of between at or about 200 μm or 300 μm to at or about 900 μm in diameter. In certain frequent embodiments, each of the plurality of apertures is defined by an aperture size of between at or about 200 μm or 300 μm to at or about 1000 μm in diameter. In certain frequent embodiments, each of the plurality of apertures is defined by an aperture size of between at or about 700 μm to at or about 900 μm in diameter. In certain frequent embodiments, each of the plurality of apertures is defined by an aperture size of between at or about 350 μm to at or about 750 μm in diameter. In certain frequent embodiments, each of the plurality of apertures is defined by an aperture size of between at or about 200 μm to at or about 1000 μm in diameter. Often in such embodiments, at least about 50% of the plurality of apertures have the identified size. Often in such embodiments, at least about 60% of the plurality of apertures have the identified size. Often in such embodiments, at least about 70% of the plurality of apertures have the identified size. Often in such embodiments, at least about 80% of the plurality of apertures have the identified size. Frequently in such embodiments, at least about 90% of the plurality of apertures have the identified size. Often in such embodiments, at least about 99% of the plurality of apertures have the identified size. When referring to "diameter" this term is referring to circular apertures and importantly is also intended to relate to the widest measurable opening (measured across the aperture opening) in the variety of non-circular shape apertures contemplated herein. So, in this sense, the term "diameter" is intended herein to have a non-conventional meaning that includes a measurement across the widest part of an opening of any shape.

In certain embodiments, the aperture size is greater than 1000 μm in diameter. In certain frequent embodiments, each of the plurality of apertures is defined by an aperture size of between at or about 1000 μm to at or about 1500 μm in diameter. In certain frequent embodiments, each of the plurality of apertures is defined by an aperture size of between at or about 1500 μm to at or about 2000 μm in diameter. In certain frequent embodiments, each of the plurality of apertures is defined by an aperture size of between at or about 2000 μm to at or about 5000 μm in diameter. In certain frequent embodiments, each of the plurality of apertures is defined by an aperture size of between at or about 5000 μm to at or about 10,000 μm in diameter. Often in such embodiments, at least about 50% of the plurality of apertures have the identified size. Often in such embodiments, at least about 60% of the plurality of apertures have the identified size. Often in such embodiments, at least about 70% of the plurality of apertures have the identified size. Often in such embodiments, at least about 80% of the plurality of apertures have the identified size. Frequently in such embodiments, at least about 90% of the plurality of apertures have the identified size. Often in such embodiments, at least about 99% of the plurality of apertures have the identified size.

When viewed on two axes, the distances between apertures is understood as an aperture density in the matrix. The aperture density is defined by the number of apertures per square centimeter. In frequent embodiments the aperture density is between 1 to 100. In certain embodiments, the aperture density is less than 1. In certain other embodiments, the aperture density is greater than 100. In certain embodiments, the aperture density is between 1 to 50. In certain embodiments, the aperture density is between 1 to 90. In certain embodiments, the aperture density is between 10 to 90. In certain embodiments, the aperture density is between 20 to 90. In certain embodiments, the aperture density is between 30 to 90. In certain embodiments, the aperture density is between 40 to 90. In certain embodiments, the aperture density is between 50 to 90. In certain embodiments, the aperture density is between 60 to 95. In certain embodiments, the aperture density is between 70 to 95. In certain embodiments, the aperture density is between 20 to 80. In certain embodiments, the aperture density is between 10 to 80. In certain embodiments, the aperture density is between 10 to 70. In certain embodiments, the aperture density is between 10 to 60. In certain embodiments, the aperture density is between 10 to 50. In certain embodiments, the aperture density is between 20 to 70. In certain embodiments, the aperture density is between 30 to 80. In certain embodiments, the aperture density is between 30 to 70. In certain embodiments, the aperture density is at or about 1, 5, 10, 15, 20, 25, 30, 35, 40, 45, 50, 55, 60, 65, 70, 75, 80, 85, 90, 95, or 100.

The aperture size may vary from the specific ranges specified herein with the proviso that the fill material is retained in the pouch without escaping through the apertures. In this regard the aperture size may often be adapted to correlate with the particle size of the fill material such that the fill material particle size is larger than the aperture size. In certain embodiments, 100% of the fill material particles are larger than the aperture size in the pouch or fibrous matrix material. In certain embodiments, 95% of the fill material particles are larger than the aperture size in the pouch or fibrous matrix material. In certain embodiments, 90% of the fill material particles are larger than the aperture size in the pouch or fibrous matrix material. In certain embodiments, 85% of the fill material particles are larger than the aperture size in the pouch or fibrous matrix material. In certain embodiments, 80% of the fill material particles are larger than the aperture size in the pouch or fibrous matrix material. In certain embodiments, 75% of the fill material particles are larger than the aperture size in the pouch or fibrous matrix material. In certain embodiments, 70% of the fill material particles are larger than the aperture size in the pouch or fibrous matrix material. In certain embodiments, 65% of the fill material particles are larger than the aperture size in the pouch or fibrous matrix material. In certain embodiments, 60% of the fill material particles are larger than the aperture size in the pouch or fibrous matrix material. When referring to the particle size of the fill material, this is intended to be a broad reference, referring to diameter of circular particles, and the narrowest profile section of all other fill materials that are not circular in shape.

In certain frequently included embodiments, each of the plurality of apertures is circular in shape. In certain frequently included embodiments, each of the plurality of apertures is oval in shape. In certain frequently included embodiments, each of the plurality of apertures is triangle in shape. In certain frequently included embodiments, each of the plurality of apertures is square in shape. In certain frequently included embodiments, each of the plurality of apertures is rectangle in shape. In certain frequently included embodiments, each of the plurality of apertures is pentagonal, hexagonal, heptagonal, or octagonal in shape. In certain frequently included embodiments, each of the plurality of apertures is polygonal in shape. In certain frequently included embodiments, each of the plurality of apertures is non-polygonal in shape. In certain frequently included embodiments, each of the plurality of apertures is either polygonal or non-polygonal in shape. In certain frequently included embodiments, the pouch comprises a plurality of apertures, where the apertures are not the same shape. In such embodiments, two or more different shaped apertures are including, including one or more different polygonal shapes and/or one or more different non-polygonal shapes. In related embodiments, each of the plurality of apertures is selected from oval, circular, square, rectangular, or another polygon shape or non-polygon shape, where two or more apertures in the pouch are differently shaped.

According to related embodiments herein, the cannabinoid containing fill material comprises cannabidiol, coconut coir, a terpene, a natural oil, a sweetener, a stabilizer and a flavorant. According to other related embodiments herein, the cannabinoid containing fill material comprises tetrahydrocannabinol, coconut coir, a terpene, a natural oil, a sweetener, a stabilizer and a flavorant.

Often, the fill material is comprised fill material particles having a mean size range of between about 800 μm to at or about 900 μm. Also often, the fill material is comprised of fill material particles having a mean size range of between about 200 μm to at or about 900 μm. As noted herein, coconut coir being a fill material contemplated in the present disclosure, it is provided in the variety of fil material sizes contemplated herein. In this regard, the particle size of the fill material (coconut coir or another fill material) is larger than the diameter of the aperture size of the matrix material of the pouch.

According to frequent embodiments, the cannabinoid containing fill material comprises water dispersible cannabidiol and/or cannabidiol isolate.

In certain frequent embodiments, the plurality of apertures comprises holes extending through the fibrous matrix material.

In certain embodiments the cannabinoid containing fill material comprises an electrospun nanofiber, wherein the electrospun nanofiber comprises cannabidiol.

Often according to the embodiments of the present disclosure, the cannabinoid containing fill material comprises a cannabinoid selected from the group consisting of one or more of cannabidiol (CBD); cannabinol; cannabigerol; cannabichromene; cannabidivarol; tetrahydrocannabidiol (i.e., Δ9-tetrahydrocannabinol); tetrahydrocannabigerol; tetrahydrocannabichromene; tetrahydrocannabidivarol; $\Delta^8$-THC, and carboxylic acid precursors of the foregoing. This list is exemplary and intended not to be limited to the specifically-listed cannabinoids. Instead, the present disclosure contemplates the full complement of *Cannabis*-derived cannabinoids, including their natural and synthetic equivalents.

Also often according to the embodiments of the present disclosure, the cannabinoid containing fill material comprises a terpene selected from the group consisting of one or more of borneol, caryophyllene, cineole/eucalyptol, delta3carene, limonene, linolool, myrcene, pinene, pulegone, d-limonene linalool, 1,8-cineole (eucalyptol), terpineol-4-ol, p-cymene, Δ-3-carene, β-sitosterol, or β-caryophyllene.cannflavin A, apigenin, and quercetin. This list is exemplary and intended not to be limited to the specifically-listed terpenes. Instead, the present disclosure contemplates the full complement of *Cannabis*-derived terpenes, including their natural and synthetic equivalents.

In certain embodiments, the cannabinoid containing fill material comprises a blended composition having a total weight, and cannabinoid containing fill material includes a cannabinoid between at or about 1% to at or about 20% of the total weight of the fill material in a bulk batch or within an exemplary pouch. In certain embodiments, the cannabinoid containing fill material comprises a blended composition having a total weight, and cannabinoid containing fill material includes a cannabinoid between at or about 5% to at or about 20% of the total weight of the fill material in a bulk batch or within an exemplary pouch. In certain embodiments, the cannabinoid containing fill material comprises a blended composition having a total weight, and cannabinoid containing fill material includes a cannabinoid between at or about 10% to at or about 20% of the total weight of the fill material in a bulk batch or within an exemplary pouch. In certain embodiments, the cannabinoid containing fill material comprises a blended composition having a total weight, and cannabinoid containing fill material includes a cannabinoid between at or about 15% to at or about 20% of the total weight of the fill material in a bulk batch or within an exemplary pouch. In certain embodiments, the cannabinoid containing fill material comprises a blended composition having a total weight, and cannabinoid containing fill material includes a cannabinoid between at or about 5%, 10% or 15% to at or about 30% of the total weight of the fill material in a bulk batch or within an exemplary pouch. In certain embodiments, the cannabinoid containing fill material comprises a blended composition having a total weight, and cannabinoid containing fill material includes a cannabinoid between at or about 5%, 10% or 15% to at or about 40% of the total weight of the fill material in a bulk batch or within an exemplary pouch. In certain embodiments, the cannabinoid containing fill material comprises a blended composition having a total weight, and cannabinoid containing fill material includes a cannabinoid between at or about 5%, 10% or 15% to at or about 50% of the total weight of the fill material in a bulk batch or within an exemplary pouch. In certain embodiments, the cannabinoid containing fill material comprises a blended composition having a total weight, and cannabinoid containing fill material includes a cannabinoid between at or about 5%, 10% or 15% to at or about 60% of the total weight of the fill material in a bulk batch or within an exemplary pouch. In certain embodiments, the cannabinoid containing fill material comprises a blended composition having a total weight, and cannabinoid containing fill material includes a cannabinoid between at or about 5%, 10% or 15% to at or about 70% of the total weight of the fill material in a bulk batch or within an exemplary pouch. In certain embodiments, the cannabinoid containing fill material comprises a blended composition having a total weight, and cannabinoid containing fill material includes a cannabinoid between at or about 5%, 10% or 15% to at or about 80% of the total weight of the fill material in a bulk batch or within an exemplary pouch. In certain embodiments, the cannabinoid containing fill material comprises a blended composition having a total weight, and cannabinoid containing fill material includes a cannabinoid between at or about 5%, 10% or 15% to at or about 90% of the total weight of the fill material in a bulk batch or within an exemplary pouch. In certain embodiments, the cannabinoid containing fill material comprises a blended composition having a total weight, and cannabinoid containing fill material includes a cannabinoid between at or about 5%, 10% or 15% to at or about 100% of the total weight of the fill material in a bulk batch or within an exemplary pouch. In certain embodiments, the cannabinoid containing fill material comprises a blended composition having a total weight, and cannabinoid containing fill material includes a cannabinoid between at or about 1% or about 100% of the total weight of the fill material in a bulk batch or within an exemplary pouch. In certain embodiments, the cannabinoid containing fill material comprises a blended composition having a total weight, and cannabinoid containing fill material includes a cannabinoid between at or about 1% to at or about 5% of the total weight of the fill material in an exemplary pouch. In certain embodiments, the cannabinoid containing fill material comprises a blended composition having a total weight, and cannabinoid containing fill material includes a cannabinoid at or about 2% of the total weight of the fill material in an exemplary pouch. In certain embodiments, the cannabinoid containing fill material comprises a blended composition having a total weight, and cannabinoid containing fill material includes a cannabinoid at or about 3% of the total weight of the fill material in an exemplary pouch. In certain embodiments, the cannabinoid containing fill material comprises a blended composition having a total weight, and cannabinoid containing fill material includes a cannabinoid at or about 4% of the total weight of the fill material in an exemplary pouch. In certain embodiments, the cannabinoid containing fill material comprises a blended composition having a total weight, and cannabinoid containing fill material includes a cannabinoid at or about 5% of the total weight of the fill material in an exemplary pouch.

In certain frequent embodiments, the fibrous matrix material comprises viscose, cellulose, polyester, cotton, hemp, cellulose acetate, polylactic acid, polypropylene, modal cellulose, Tencel, or blends of two or more of the foregoing.

In certain frequent embodiments, the cannabinoid containing fill material comprises coconut coir, CBD distillate, a terpene, a natural oil, a sweetener, salt, and a stabilizer within an apertured matrix pouch.

In certain frequent embodiments, the cannabinoid containing fill material comprises an absorbent natural fiber selected from one or more of coconut coir, kenaf, abaca, flax, hemp, jute, ramie, sisal, rice, bamboo, corn husk, siH husk, fruit skin, straw, soy, mint leaf, spearmint leaf, lettuce leaf, synthetic fibers, animal-derived fibers, chitin, kudzu root, or a combination of two or more of the foregoing; a cannabinoid selected from one or more of cannabidiol (CBD); cannabinol; cannabigerol; cannabichromene; cannabidivarol; tetrahydrocannabidiol; tetrahydrocannabigerol; tetrahydrocannabichromene; tetrahydrocannabidivarol; $\Delta^8$-THC, and/or carboxylic acid precursors of the foregoing; in addition to other related compounds and their derivatives; a terpene selected from one or more of borneol, caryophyllene, cineole/eucalyptol, delta3carene, limonene, linolool, myrcene, pinene, pulegone, d-limonene linalool, 1,8-cineole (eucalyptol), terpineol-4-ol, p-cymene, $\Delta$-3-carene, $\beta$-sitosterol, or $\beta$-caryophyllene.cannflavin A, apigenin, quercetin or the like; a natural oil selected from one or more of vegetable oil, peanut oil, canola oil, sunflower oil, palm oil, walnut oil, safflower oil, grapeseed oil, flaxseed oil, avocado oil, coconut oil, olive oil, and the like; a sweetener selected from one or more of a sugar, glycerine, corn syrup, stevia, acesulfame potassium, aspartame, cyclamate, mogrosides, sucralose, maltodextrin, a sugar alcohol, and the like; salt, a thickening agent or stabilizer selected from one or more of xanthum gum, an alginate, agar, carrageen, cellulose and cellulose derivatives, gelatin, guar gum, gum Arabic, locust bean gum, pectin, a starch, carrageenan, pectin, gelatin, a sulfonate, and the like; and a flavorant selected from one or more of spearmint, corn mint, herbal mint, peppermint, wintergreen, citrus grove, orange, lime, lemon, tangerine, mandarin, coffee flavor, espresso oil, spiced cayenne oil, mango, cinnamon, and other natural and artificial flavors within a apertured matrix pouch.

The adaptations provided in the matrix material permit pouches formed therefrom to release the cannabinoid and/or terpene from the fill material faster than the same matrix material without apertures. Often such a release rate permits 30%, 40%, 50%, 60%, 70%, 80%, 90%, or 100% of the cannabinoid and/or terpene from the pouch in 3, minutes, 4, minutes, 5, minutes, 6 minutes, 7, minutes, 8, minutes, 9, minutes, 10 minutes, 11, minutes, 12, minutes, 13, minutes, 14 minutes, 15, minutes, 16, minutes, 17, minutes, 18 minutes, 19 minutes or 20 minutes. Often such a release rate permits 30%, 40%, 50%, 60%, 70%, 80%, 90%, or 100% of the cannabinoid and/or terpene from the pouch in between 3 minutes to 20 minutes. Often such a release rate permits 30%, 40%, 50%, 60%, 70%, 80%, 90%, or 100% of the cannabinoid and/or terpene from the pouch in between 5 minutes to 15 minutes. Often such a release rate permits 30%, 40%, 50%, 60%, 70%, 80%, 90%, or 100% of the cannabinoid and/or terpene from the pouch in between 5 minutes to 10 minutes. Often such a release rate permits 30%, 40%, 50%, 60%, 70%, 80%, 90%, or 100% of the cannabinoid and/or terpene from the pouch in between 3 minutes to 20 minutes. Often such a release rate permits 30%, 40%, 50%, 60%, 70%, 80%, 90%, or 100% of the cannabinoid and/or terpene from the pouch in between 3 minutes to 15 minutes.

Kits comprising a plurality of pouches for administration of a cannabinoid as described herein contained within a sealed container are also included in the contemplated embodiments. Often this sealed container is a container that is sealed such that it prohibits entry of gas and liquid into the interior of the container when closed and sealed.

These and other embodiments, features, and advantages will become apparent to those skilled in the art when taken with reference to the following more detailed description of various exemplary embodiments of the present disclosure in conjunction with the accompanying drawings.

BRIEF DESCRIPTION OF THE DRAWINGS

The skilled person in the art will understand that the drawings, described below, are for illustration purposes only.

FIG. 2A depicts a side view of an exemplary pouch. FIG. 2B depicts a front view of an exemplary pouch. FIG. 2C depicts a rear view of an exemplary pouch.

DETAILED DESCRIPTION

Figure 1:
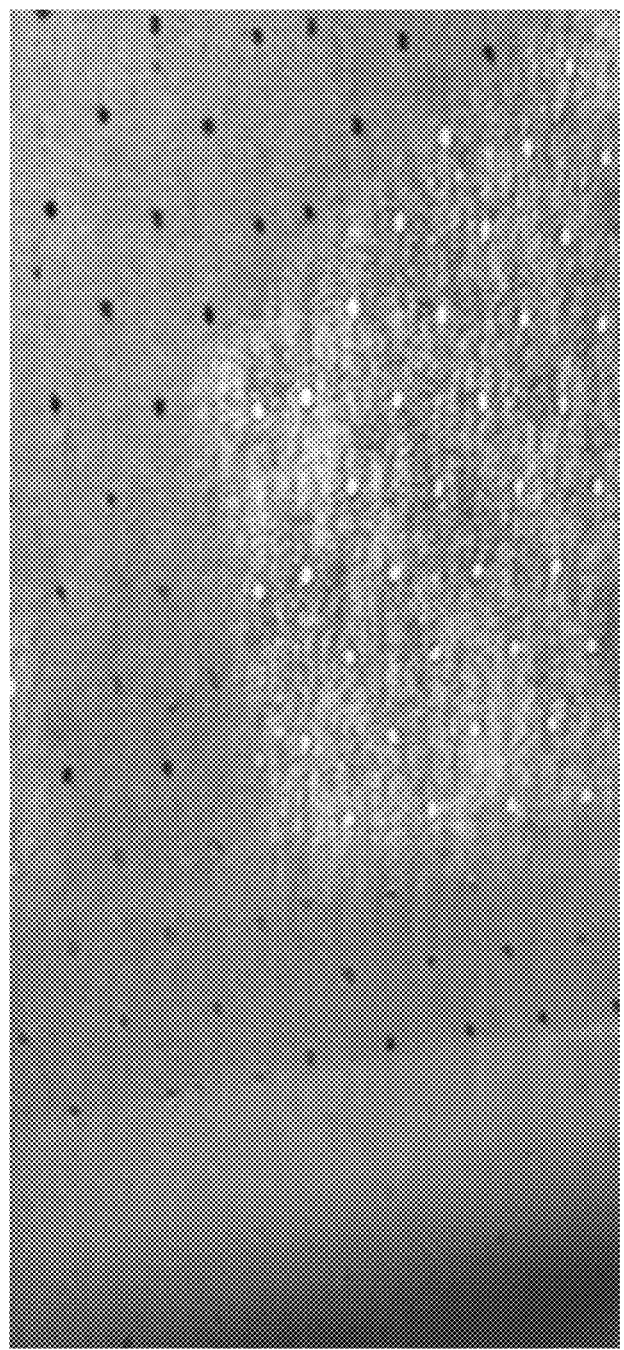
FIG. 1 depicts a photo of an exemplary fibrous matrix material including apertures according to the present disclosure.

For clarity of disclosure, and not by way of limitation, the detailed description of the invention is divided into the subsections that follow.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more." As such, "a" is intended to refer to a single unit as well as a plurality of units.

As used herein, the term "and/or" may mean "and," it may mean "or," it may mean "exclusive-or," it may mean "one," it may mean "some, but not all," it may mean "neither," and/or it may mean "both."

As used herein, "aperture" refers to a hole or opening in a fibrous matrix material. In certain defined embodiments, "aperture" refers to a hole or opening in a fibrous matrix material that is of a different character than a gap between fibers in a woven or nonwoven fabric material. In these specific embodiments, naturally existing gaps between fibers within a weave or mat of a woven or nonwoven fabric material are excluded from the meaning of "aperture" as this term is used herein.

As used herein, "cannabinoids" refers to a family of natural products that usually contain a 1,1'-di-methyl-pyrane ring, a variedly derivatized aromatic ring and a variedly unsaturated cyclohexyl ring and their immediate chemical precursors.

Examples of cannabinoids contemplated here include cannabidiol (CBD); cannabinol; cannabigerol; cannabichromene; cannabidivarol; tetrahydrocannabidiol; tetrahydrocannabigerol; tetrahydrocannabichromene; tetrahydrocannabidivarol; $\Delta^8$-THC; carboxylic acid precursors of the foregoing; in addition to other related compounds and their derivatives. Cannabidiol (CBD), is one of at least 113 known phytocannabinoids found in the *Cannabis* plant. CBD is one of the major phytocannabinoids in the *Cannabis* plant, comprising a up to 40% of extracts.

As used herein, "terpene" refers to borneol, caryophyllene, cineole/eucalyptol, delta3carene, limonene, linolool, myrcene, pinene, or pulegone, among other terpenes, which are a diverse group of organic hydrocarbons that are the building blocks of the cannabinoids. Certain examples include d-limonene linalool, 1,8-cineole (eucalyptol), α-pinene, terpineol-4-ol, p-cymene, borneol, Δ-3-carene, β-sitosterol, β-myrcene, or β-caryophyllene.cannflavin A, apigenin, quercetin or pulegone. Over 100 different terpenes have been identified in the *Cannabis* plant and while examples are noted above, these are non-limiting examples of the over 100 known terpenes contemplated herein.

*Cannabis* is a genus of flowering plants that includes three different species, *Cannabis sativa, Cannabis* indica and *Cannabis ruderalis*. The term "*Cannabis* plant(s)" encompasses wild type *Cannabis* and also variants thereof, including *Cannabis* chemovars which naturally contain different amounts of the individual cannabinoids. *Cannabis* plants produce a unique family of terpeno-phenolic compounds called cannabinoids, which produce psychoactive effects. The two cannabinoids usually produced in greatest abundance are cannabidiol (CBD) and/or Δ9-tetrahydrocannabinol (THC), but only THC is psychoactive. *Cannabis* plants are categorized by their chemical phenotype or "chemotype," based on the overall amount of THC produced, and on the ratio of THC to CBD. Although overall cannabinoid production is influenced by environmental factors, the THC/CBD ratio is genetically determined and remains fixed throughout the life of a plant. Non-drug plants produce relatively low levels of THC and high levels of CBD, while drug plants produce high levels of THC and low levels of CBD.

Cannabinoids are fat soluble and poorly soluble to insoluble in water. Poor aqueous solubility of many chemical entities represents a real challenge for the design of appropriate formulations aimed at enhancing oral bioavailability. By contrast, nicotine is a weak base (pKa of 8.0), it is primarily present in a non-ionised form in alkaline pH; thus nicotine is easily absorbed at normal to increased pH levels which are normal saliva conditions (Ciolino et al., J. Analytical Toxicol. 25:15-25 (2001)).

The isolation of cannabidiol from red oil obtained from hemp was initially described by Adams et al., J.A.C.S. 62:196-200 (1940); U.S. Pat. No. 2,304,669. This process involved treatment of purified oil with 3,5-dinitrobenzoyl chloride and the formation of cannabidiol bis-3,5-dinitrobenzoate. Ammonolysis of the benzoate yielded cannabidiol in pure form.

A variety of other solvent-based cannabinoid extraction and separation techniques are known in the art to purify cannabinoid from the *Cannabis* plant and separate cannabinoid from $\Delta^9$-THC.

The present disclosure provides cannabinoid-containing pouches formed of a nonwoven or woven fiber matrix and characterized by the presence of apertures and methods of manufacturing such pouches.

A fill material is included in the exemplary pouches of the present disclosure. This fill material frequently comprises at least one cannabinoid as an active component. This fill material also often frequently includes at least one terpene as an active component. This fill material also often comprises at least one additional ingredient that imparts a flavor and/or an aroma as an active component. This fill material also often comprises at least one cannabinoid, at least one terpene, and an additional ingredient that imparts a flavor and an aroma as active components. This fill material also often comprises at least one cannabinoid and an additional ingredient that imparts a flavor and an aroma as active components. This fill material also often comprises at least one terpene and an additional ingredient that imparts a flavor and an aroma as active components.

In frequently included embodiments, the fill material comprises a ground base material that is dosed, infused or combined with an active component. Often this fill material comprises coconut coir, which is the pith component of the coconut between the hard internal shell and the outer coat of the coconut. When included, this base material is often included at a predetermined particulate size, which size is generally larger than the apertures in the matrix of the pouch. In certain exemplary embodiments, the fill material is a ground material such as ground coconut coir. Coconut coir has been surprisingly found by the inventors to have both a very absorbent nature and a relaxed release characteristic for the active components described herein. The fill material can be large or small particulate material, threads, fibers, slices, or another shape of a piece (or collection of pieces) of the core base material. Also often, the fill material is kenaf. Also often, the fill material is abaca. Also often, the fill material is flax. Also often, the fill material is hemp. Also often, the fill material is jute. Also often, the fill material is ramie. Also often, the fill material is sisal. Also often, the fill material is rice. Also often, the fill material is bamboo. Also often, the fill material is corn husk. Also often, the fill material is silk husk. Also often, the fill material is fruit skin. Also often, the fill material is straw. Also often, the fill material is soy. Also often, the fill material is mint leaf. Also often, the fill material is spearmint leaf. Also often, the fill material is lettuce leaf. Also often, the fill material is comprised of synthetic fibers. Also often, the fill material is comprised of animal-derived fibers. Also often, the fill material is comprised of kudzu root. Therefore, the fill material of the present disclosure can be large or small particulate material, threads, fibers, slices, or another shape of a piece (or collection of pieces) of the core base material, which base material is selected from one or more of the following: coconut coir, kenaf, abaca, flax, hemp, jute, ramie, sisal, rice, bamboo, corn husk, silk husk, fruit skin, straw, soy, mint leaf, spearmint leaf, lettuce leaf, synthetic fibers, animal-derived fibers, chitin, and kudzu root.

In certain embodiments the base material, such as coconut coir, is ground/milled to a mean particulate size of at or about 600 μm. Often the base material is ground to a mean particulate size of between about 800 μm to at or about 900 μm. Often the base material is ground to a mean particulate size of between about 900 μm to at or about 1500 μm. In processing different screen pore sizes may be utilized to further process the post-milled base material to ensure size consistency. For instance, in certain embodiments, the screen size is larger than the milled mean particulate size. In this regard, often the screen pore size is between about 800 µm to at or about 900 µm. Often the screen pore size is between about 900 µm to at or about 1500 µm. In certain embodiments, the base material is ground and optionally further processed to a mean particulate size of between about 600 µm to at or about 900 µm. In certain embodiments, the base material is ground and optionally further processed to a mean particulate size of between about 700 µm to at or about 800 µm. In certain embodiments, the base material is ground and optionally further processed to a mean particulate size of between about 800 µm to at or about 2000 µm. In certain embodiments, the base material is ground and optionally further processed to a mean particulate size of between about 900 µm to at or about 1500 µm. In related embodiments, over 50% of the base material has this particle size. More frequently, over 60% of the base material has this particle size. More frequently, over 70% of the base material has this particle size. Often, over 80% of the base material has this particle size. Also often, over 90% of the base material has this particle size. As noted, although coconut coir is exemplified, it is merely exemplary and not intended to be limiting as a base material. Other natural fibers, such as other cellulosic fibers, may be utilized. Additional materials may comprise the base material, for example the fill material comprises an absorbent natural fiber selected from one or more of coconut coir, kenaf, abaca, flax, hemp, jute, ramie, sisal, rice, bamboo, corn husk, silk husk, fruit skin straw, soy, mint leaf, spearmint leaf, lettuce leaf, synthetic fibers, animal-derived fibers, chitin, kudzu root and the like, including combinations of two or more of the foregoing. Often beneficial characteristics of suitable base materials are those that are inert, biocompatible, have strong absorbent characteristics and release active components contained within or on the base material readily when in the oral environment or contacted with liquid such as saliva.

The material ground to form the base material is often generally sterilized prior to any additional processing steps to be sure the material is free from any inherent or processing-introduced bacterial contamination.

In exemplary pouch embodiments of the present disclosure a combination of active components and base material are combined as fill materials. Though referred to as "active components" these are simply intended to refer to the collected ingredients utilized to incorporate with the base material. In certain embodiments, a CBD isolate or distillate, a terpene (often including a plurality of terpenes) is included with one or more natural oils, one or more sweeteners, a salt, a thickening agent or stabilizer, and ground coconut coir in a fill material. Also in certain embodiments, a pure form or an isolate or distillate of a cannabinoid and/or a terpene is included with one or more natural oils, one or more sweeteners, a salt, a thickening agent or stabilizer, and kenaf, abaca, flax, hemp, jute, ramie, sisal, rice, bamboo, corn husk, silk husk, fruit skin, straw, soy, mint leaf, spearmint leaf, lettuce leaf, synthetic fibers, animal-derived fibers, chitin, and/or kudzu root in a fill material.

In certain embodiments, the sweetener is often selected from one or more of a sugar, glycerine, corn syrup, stevia, acesulfame potassium, aspartame, cyclamate, mogrosides, sucralose, maltodextrin, monkfruit, erythritol, a sugar alcohol, and the like. In related embodiments, the natural oil is often selected from one or more of vegetable oil, peanut oil, canola oil, sunflower oil, palm oil, walnut oil, safflower oil, grapeseed oil, flaxseed oil, hempseed oil, avocado oil, coconut oil, olive oil, or the like.

In certain frequent embodiments, the fill material comprises an absorbent natural fiber selected from one or more of coconut coir, kenaf, abaca, flax, hemp, jute, ramie, sisal, rice, bamboo, corn husk, silk husk, fruit skin, straw, soy, mint leaf, spearmint leaf, lettuce leaf, synthetic fibers, animal-derived fibers, chitin, kudzu root and the like; a cannabinoid selected from one or more of cannabidiol (CBD); cannabinol; cannabigerol; cannabichromene; cannabidivarol; tetrahydrocannabidiol; tetrahydrocannabigerol; tetrahydrocannabichromene; tetrahydrocannabidivarol; $\Delta^8$-THC; carboxylic acid precursors of the foregoing; in addition to other related compounds and their derivatives; a terpene selected from one or more of borneol, caryophyllene, cineole/eucalyptol, delta3carene, limonene, linlool, myrcene, pinene, pulegone, d-limonene linalool, 1,8-cineole (eucalyptol), terpineol-4-ol, p-cymene, $\Delta$-3-carene, $\beta$-sitosterol, or $\beta$-caryophyllene.cannflavin A, apigenin, quercetin or the like; a natural oil selected from one or more of vegetable oil, peanut oil, canola oil, sunflower oil, palm oil, walnut oil, safflower oil, grapeseed oil, flaxseed oil, avocado oil, coconut oil, olive oil, and the like; a sweetener selected from one or more of a sugar, glycerine, corn syrup, stevia, acesulfame potassium, aspartame, cyclamate, mogrosides, sucralose, maltodextrin, a sugar alcohol, and the like; salt, a thickening agent or stabilizer selected from one or more of xanthum gum, an alginate, agar, carrageen, cellulose and cellulose derivatives, gelatin, guar gum, gum Arabic, locust bean gum, pectin, a starch, carrageenan, pectin, gelatin, a sulfonate, and the like; and a flavorant selected from one or more of spearmint, corn mint, herbal mint, peppermint, wintergreen, citrus grove, orange, lime, lemon, tangerine, mandarin, coffee flavor, espresso oil, spiced cayenne oil, mango, cinnamon, and other natural and artificial flavors within a apertured matrix pouch. In certain frequent embodiments, the fill material comprises coconut coir, CBD distillate, a terpene, a natural oil, a sweetener, salt, and a stabilizer within an apertured matrix pouch.

In certain frequent embodiments, the active component(s) comprises at or about 5% to at or about 20% w/w of the total fill material of the apertured pouch. In certain frequent embodiments, the active component(s) comprises between about 9%-11% of the total fill material of the apertured pouch. In certain frequent embodiments, the active component(s) comprises at or about 10% of the total fill material of the apertured pouch. In certain frequent embodiments, the active component(s) comprises at or about 5%, 6%, 7%, 8%, 9%, 10%, 11%, 12%, 13%, 14%, 15%, 16%, 17%, 18%, 19%, or 20% of the total fill material of the apertured pouch. In certain frequent embodiments, the active component(s) active component(s) comprises above 20% of the total fill material of the apertured pouch, though in such embodiments the cannabinoid often comprises a non-isolated or non-concentrated form of cannabinoid. In certain frequent embodiments the cannabinoid comprises water dispersible CBD. In other embodiments the cannabinoid comprises naturally occurring CBD. In other embodiments the cannabinoid comprises a blend of water dispersible CBD and naturally occurring CBD.

In certain embodiments the natural oil comprises at or about 5% to at or about 20% w/w of the total fill material of the apertured pouch. Often the natural oil is incorporated in the fill material at or about the same concentration of the active component(s).

In one exemplary embodiment, the active component(s) (e.g., CBD) is mixed with maltodextrin, sunflower lecithin and the resulting emulsion is dried to remove water. This formulation is often used in exemplary embodiments to incorporate into coconut coir for the fill material. In certain embodiments, this fill material is further processed to blend in and incorporate additional ingredients such as an additional oil, salt, a sweetener, a terpene, a flavorant, and a stabilizer, then left to cure for a period of time prior to filling an exemplary pouch. Curing time often varies but is frequently between 24 hours to 72 hours. In certain embodiments, the curing time is at or about 48 hours.

According to the present disclosure the matrix material is prepared and shaped into a pouch by bending a flat sheet of matrix material into a U-shape, sealing the sides of the "U" to create a tube, sealing one lateral edge of the tube to create an open-topped pocket, and then sealing the open top after a fill material is introduced to the pocket. This process, including matrix material preparation, aperture introduction to the matrix material, sizing/sectioning of the apertured matrix material into a size for pouch formation, movement of raw materials, formation of the apertured matrix material pocket, filling the apertured matrix material pocket and sealing the pocket to form an apertured pouch of the present disclosure may be manual or automated. This process is most frequently automated. The matrix material sealing process to form the "U" and then closure of the top is often dependent on the type of material forming the matrix, though combined heat and pressure is a preferred method. The portion of the sheet of matrix material forming an exemplary pouch that is used to form the seal on the two or more (e.g., 3 or 4) sides of the eventual pouch is referred to herein as the sealing lip of the matrix material.

Materials useful in forming the matrix include viscose, cellulose, polyester, cotton, hemp, cellulose acetate, polylactic acid, polypropylene, modal cellulose, Tencel, or another material. A variety of additional materials may be utilized with the caveat that such materials are non-reactive and/or do not degrade in the oromucosal environment.

The aperture size in the matrix material of the exemplary pouches often will range from between about 400 µm to about 800 µm in diameter. In the most frequent embodiments, the aperture is a circular aperture. In certain embodiments, the aperture size ranges between about 500 µm to about 800 µm in diameter. In certain embodiments, the aperture size ranges between about 600 µm to about 800 µm in diameter. In certain embodiments, the aperture size ranges between about 700 µm to about 800 µm in diameter. In certain embodiments, the aperture size ranges between about 600 µm to about 700 µm in diameter. In certain embodiments, the aperture size ranges between about 400 µm to about 600 µm in diameter. In certain embodiments, the aperture size in the matrix material of the exemplary pouches ranges between about 750 µm to about 850 µm in diameter. In certain embodiments, the aperture size in the matrix material of the exemplary pouches is about 800 µm in diameter. In certain embodiments, the aperture size is greater than 1000 µm in diameter. In certain frequent embodiments, each of the plurality of apertures is defined by an aperture size of between at or about 1000 µm to at or about 1500 µm in diameter. In certain frequent embodiments, each of the plurality of apertures is defined by an aperture size of between at or about 1500 µm to at or about 2000 µm in diameter. In certain frequent embodiments, each of the plurality of apertures is defined by an aperture size of between at or about 2000 µm to at or about 5000 µm in diameter. In certain frequent embodiments, each of the plurality of apertures is defined by an aperture size of between at or about 5000 µm to at or about 10,000 µm in diameter. In certain embodiments, the aperture size of at least 50% of the apertures present in the matrix material of the exemplary pouches is at or about 400 µm in diameter, at or about 450 µm in diameter, at or about 500 µm in diameter, at or about 550 µm in diameter, at or about 600 µm in diameter, at or about 650 µm in diameter, at or about 700 µm in diameter, at or about 750 µm in diameter, at or about 800 µm in diameter, at or about 850 µm in diameter, at or about 900 µm in diameter, at or about 950 µm in diameter, at or about 1000 µm in diameter, at or about 425 µm in diameter, at or about 475 µm in diameter, at or about 525 µm in diameter, at or about 575 µm in diameter, at or about 625 µm in diameter, at or about 675 µm in diameter, at or about 725 µm in diameter, at or about 775 µm in diameter, at or about 825 µm in diameter, at or about 875 µm in diameter, at or about 925 µm in diameter, at or about 975 µm in diameter. In certain embodiments, the aperture size of at least 50% of the apertures present in the matrix material of the exemplary pouches is at or about 1000 µm in diameter, between at or about 1000 µm to at or about 1500 µm in diameter, between at or about 1500 µm to at or about 2000 µm in diameter, between at or about 2000 µm to at or about 5000 µm in diameter, or between at or about 5000 µm to at or about 10,000 µm in diameter. In certain related embodiments, the above-noted aperture size is for at least 60% of the apertures present in the matrix material of the exemplary pouches. In certain related embodiments, the above-noted aperture size is for at least 70% of the apertures present in the matrix material of the exemplary pouches. In certain related embodiments, the above-noted aperture size is for at least 75% of the apertures present in the matrix material of the exemplary pouches. In certain related embodiments, the above-noted aperture size is for at least 80% of the apertures present in the matrix material of the exemplary pouches. In certain related embodiments, the above-noted aperture size is for at least 85% of the apertures present in the matrix material of the exemplary pouches. In certain related embodiments, the above-noted aperture size is for at least 90% of the apertures present in the matrix material of the exemplary pouches. In certain related embodiments, the above-noted aperture size is for at least 95% of the apertures present in the matrix material of the exemplary pouches. In certain related embodiments, the above-noted aperture size is for at least 100% of the apertures present in the matrix material of the exemplary pouches.

In certain embodiments the pouch is comprised of a matrix material that contains apertures on at least one side or portion and another portion of matrix material that lacks defined apertures. In certain embodiments the pouch includes a section with apertures and a section that lacks apertures. Often in such embodiments, the pouch is adapted for use or specific placement in the mouth of a user, including the portion or side of the pouch having apertures facing away from the oromucosal surface. In such an embodiment, the portion of the pouch that lacks apertures may be contacting or facing the oromucosal surface. Alternatively, in other embodiments, the pouch is adapted for use or specific placement in the mouth of a user, including the portion or side of the pouch having apertures facing toward, or contacting, the oromucosal surface. In such an embodiment, the portion of the pouch that lacks apertures may be facing away from not contacting the oromucosal surface.

Referring now to the drawings, a pouch formed from a fibrous matrix according to an embodiment of the present disclosure is shown in FIG. 1.

Figure 2A:
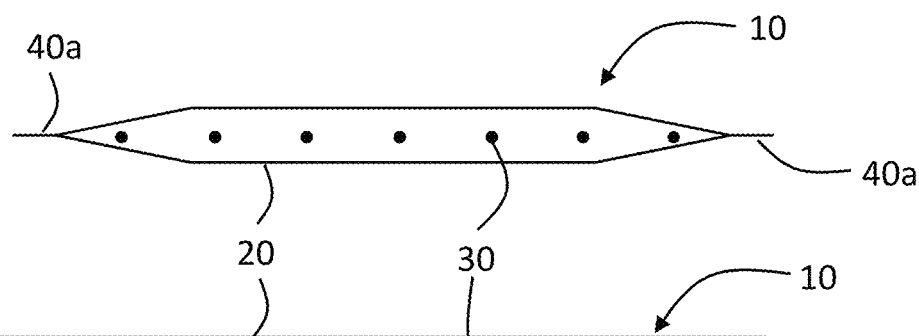
FIGS. 2A-2C depict an exemplary pouch formed of an aperture-containing fibrous matrix material.
Figure 2B:
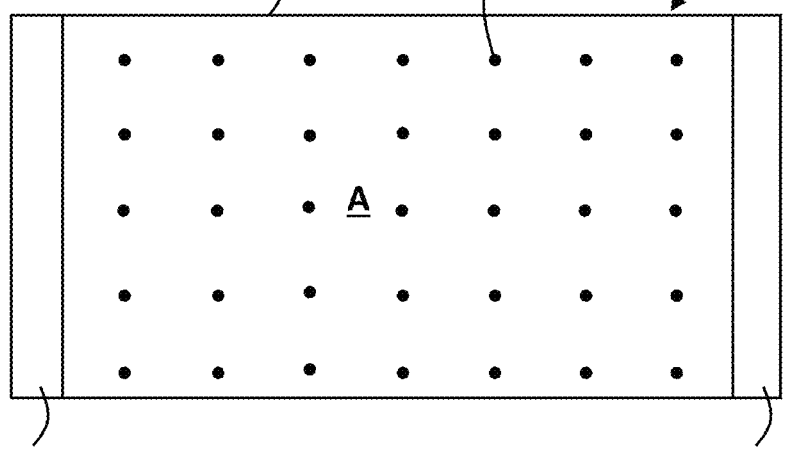
Figure 2C:
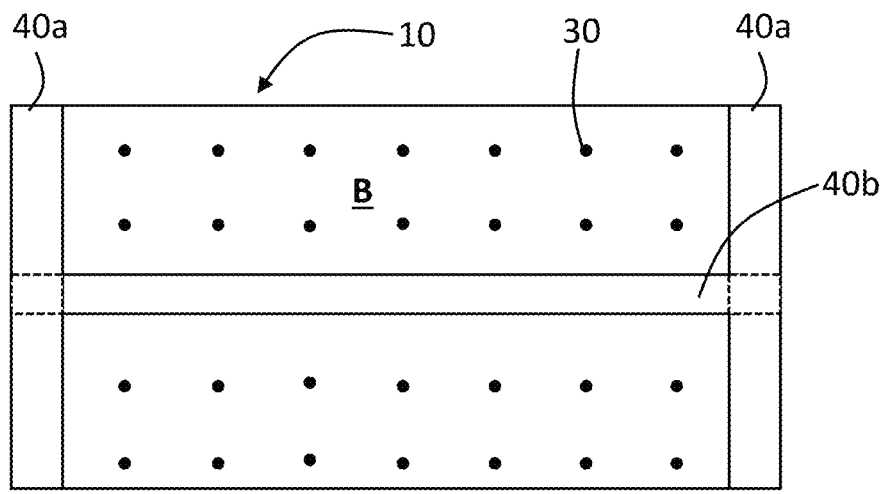

An exemplary pouch formed of the aperture-containing fibrous matrix material is depicted in FIGS. 2A-2C. FIG. 2A depicts a side view of an exemplary pouch. FIG. 2B depicts a front view of an exemplary pouch. FIG. 2C depicts a rear view of an exemplary pouch. The pouch includes a top face (A) and an opposing bottom face (B). The top face is bound with the bottom face using seals along the bottom face (40*b*) and along the opposing lateral edges (40*a*). Thus, a seal spans three sides of the pouch in frequent embodiments since the exemplary pouch is formed from a single contiguous fibrous matrix sheet. This seal is often formed by aligning folded edges (sealing lip(s)) of the fibrous matrix sheet and applying pressure and heat to the sealing lip(s). Less frequently an adhesive is used. The seal along the bottom face (40*b*) could also be shifted to an edge of the pouch instead of running down the middle of the bottom face (B). The seal along the bottom face (40*b*) is shown for example to show another manner of forming a seal between two edges of the fibrous matrix material. In practice, formation of the seal along the bottom face (40*b*) creates a tube. Sealing one of the two lateral edges (40*a*) creates a pocket. If done in sequence, sealing the other of the two lateral edges (40*a*) creates a pouch.

As described herein, the pouch generally contains fill material comprising cannabinoids. In a process of manufacturing the presently described pouches, the added step of filling the pocket with a fill material comprising a cannabinoid is included prior to sealing the other of the two lateral edges (40*a*) to create the pouch.

In the most frequent embodiments, the fibrous matrix is composed of non-woven fibers and is formed with a plurality of apertures, thus the fibrous matrix is referred to as an apertured fibrous matrix. In other embodiments, the fibrous matrix is composed of woven fibers and is formed with a plurality of apertures.

Forming the material for the fibrous matrix may be by conventional or other procedures. For example, conventional non-woven hydroentanglement processes and reagents may be used to form the fibrous matrix, thereafter the fibrous matrix is embossed to form the apertures. Plate or roll based manufacturing may be utilized.

Alternatively, the fibrous matrix may be formed of electrospun fibers. Needle or needleless electrospinning may be utilized in such methods to form at least a portion of the fibrous matrix. In other alternative embodiments, the fill material may comprise electrospun fibers such as electrospun nanofibers comprising a cannabinoid and/or a terpene contemplated herein. In practice when the electrospun nanofibers comprise a cannabinoid (e.g., CBD) and/or a terpene contemplated herein, the nanofibers are formed on what is or will become the inside of the apertured matrix material of the pouch. In such embodiments, it has been found that providing a strip/mat of nanofibers on and within the boundaries of a pre-formed apertured matrix material is suitable. Generally, the width of the nanofiber comprising the cannabinoid (e.g., CBD) is most suitable if it lies within what will be the true inside of the to-be-formed pouch such that a sealing lip of matrix material is left uncovered with nanofiber. In certain embodiments, the matrix material is at or about 40 mm in width and the electrospun nanofiber comprising the cannabinoid is about 10 mm to 20 mm in width and positioned in the center of the matrix material, leaving at or about 10 mm on two sides for use as the sealing lip. As the heat utilized to seal pouches formed with exemplary matrix materials to is often at a level that would negatively affect the integrity of cannabinoids, placement of the electrospun nanofiber comprising the cannabinoid within and outside of the sealing lip has been found to be advantageous The aperture shape is often circular. Alternatively, in other embodiments the aperture shape is a shape other than circular, including square, rectangle, oval, triangle, diamond, or another geometric shape. In the most frequent embodiments when the pouch is formed of a single sheet of fibrous matrix material the aperture shape is a single shape across the entirety of the pouch. Also often, two or more different shaped apertures are included in the same pouch. In certain frequently included embodiments, each of the plurality of apertures is pentagonal, hexagonal, heptagonal, or octagonal in shape. In certain frequently included embodiments, each of the plurality of apertures is polygonal in shape. In certain frequently included embodiments, each of the plurality of apertures is non-polygonal in shape. In certain frequently included embodiments, each of the plurality of apertures is either polygonal or non-polygonal in shape. In certain frequently included embodiments, the pouch comprises a plurality of apertures, where the apertures are not the same shape. In such embodiments, two or more different shaped apertures are including, including one or more different polygonal shapes and/or one or more different non-polygonal shapes. In related embodiments, each of the plurality of apertures is selected from oval, circular, square, rectangular, or another polygon shape or non-polygon shape, where two or more apertures in the pouch are differently shaped.

In certain embodiments the apertured fibrous matrix includes between at or about 2 mm to at or about 4 mm between apertures of an exemplary pouch. In certain embodiments the distance between apertures in the fibrous matrix of an exemplary pouch is at or about 3.5 mm. In certain embodiments, the apertured fibrous matrix of an exemplary pouch includes between at or about 1 mm to at or about 10 mm between apertures. In certain embodiments the distance between apertures of an exemplary pouch in the fibrous matrix is at or about 1.5 mm, 2.5 mm, 3.5 mm, 4.5 mm, 5.5 mm, 6.5 mm, 7.5 mm, 8.5 mm, or 9.5 mm. In certain embodiments the distance between apertures in the fibrous matrix of an exemplary pouch is at or about 2 mm, 3 mm, 4 mm, 5 mm, 6 mm, 7 mm, 8 mm, or 9 mm. In certain embodiments the apertured fibrous matrix includes a varied distance between apertures, which varied distance is at or about 2 mm to at or about 4 mm between apertures in one part of the fibrous matrix, and at or about 4 mm to at or about 10 mm in one part of the fibrous matrix of an exemplary pouch.

When viewed on two axes, the distances between apertures is understood as an aperture density in the matrix. The aperture density is defined by the number of apertures per square centimeter. In frequent embodiments the aperture density is between 1 to 100. In certain embodiments, the aperture density is less than 1. In certain other embodiments, the aperture density is greater than 100. In certain embodiments, the aperture density is between 1 to 50. In certain embodiments, the aperture density is between 1 to 90. In certain embodiments, the aperture density is between 10 to 90. In certain embodiments, the aperture density is between 20 to 90. In certain embodiments, the aperture density is between 30 to 90. In certain embodiments, the aperture density is between 40 to 90. In certain embodiments, the aperture density is between 50 to 90. In certain embodiments, the aperture density is between 60 to 95. In certain embodiments, the aperture density is between 70 to 95. In certain embodiments, the aperture density is between 20 to 80. In certain embodiments, the aperture density is between 10 to 80. In certain embodiments, the aperture density is between 10 to 70. In certain embodiments, the aperture density is between 10 to 60. In certain embodiments, the aperture density is between 10 to 50. In certain embodiments, the aperture density is between 20 to 70. In certain embodiments, the aperture density is between 30 to 80. In certain embodiments, the aperture density is between 30 to 70. In certain embodiments, the aperture density is at or about 1, 5, 10, 15, 20, 25, 30, 35, 40, 45, 50, 55, 60, 65, 70, 75, 80, 85, 90, 95, or 100.

The arrangement and the characteristics of the apertures in the apertured fibrous matrix provide a variety of advantages. For example, the apertured fibrous matrix provides an increased rate of release of cannabinoids through the apertured fibrous matrix, without a loss of substrate material contained in the pouch. Thus, cannabinoids can solubilize and pass through the apertures without loss of the substrate containing the cannabinoids.

In addition, when comparing fibrous matrix of a pouch lacking apertures with an apertured fibrous matrix, the apertured fibrous matrix is more flexible. As such, pouches comprised of apertured fibrous matrix are more conformable in the mouth of a subject using the pouch. This enhances flexibility in oromucosal placement options.

The rate of release of cannabinoid constituents (i.e., CBD, tetrahydrocannabinol, etc.) from an exemplary pouch formed from the apertured fibrous matrix was tested and compared to the rate of release of cannabinoid constituents from a pouch formed from matrix material lacking apertures. The results are set forth in FIGS. 3 and 4.

In this experiment, the following pouches were used: an exemplary pouch formed from the apertured fibrous matrix containing a known amount of water dispersible cannabinoids; and a pouch formed from matrix material lacking apertures but also containing a known amount of water dispersible cannabinoids. Multiple such pouches were prepared, each to be used in a different time duration experiment. The concentration of cannabinoid in the pouch was measured prior to placement in vivo in the oromucosal environment of a subject and at defined time periods after being placed in the oromucosal environment of the subject. For example, a pouch was placed in the mouth of the subject and removed one minute later and the cannabinoids remaining in the pouch were measured. Similarly, a different pouch was placed in the mouth of the subject and removed five minutes later and the cannabinoids remaining in the pouch were measured. Similarly, a different pouch was placed in the mouth of the subject and removed ten minutes later and the cannabinoids remaining in the pouch were measured. This process was repeated for both exemplary pouches formed from the apertured fibrous matrix cannabinoids and pouches formed from matrix material lacking apertures across the time periods noted in the Figures.

Figure 3:
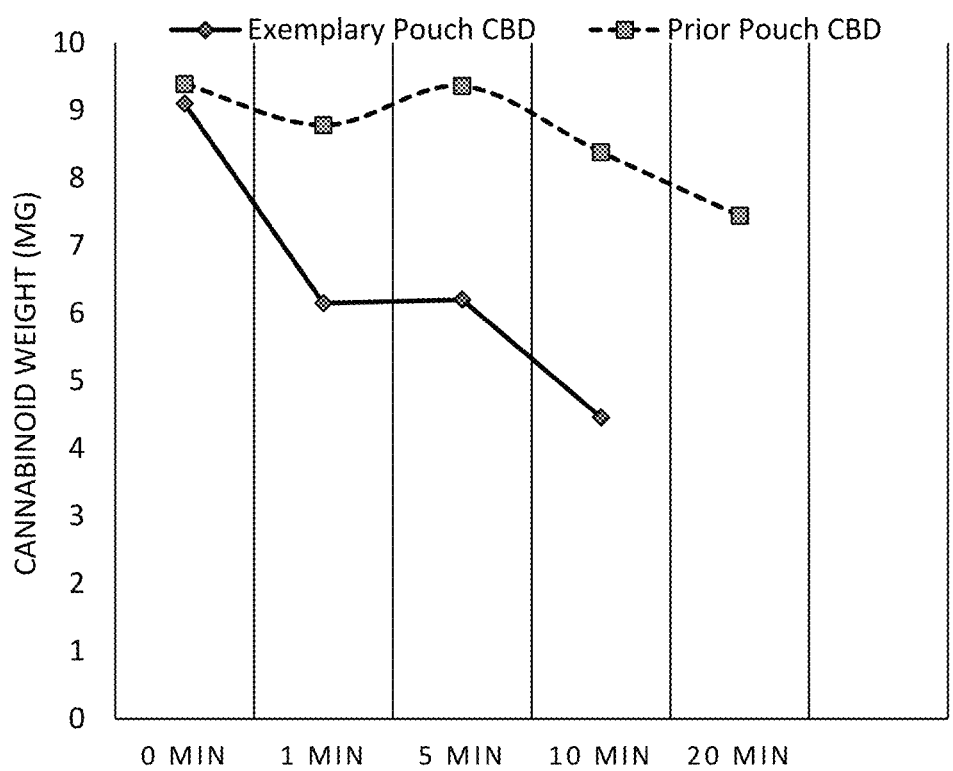
FIG. 3 depicts results showing the reduction of the cannabidiol in an exemplary pouch and a conventional pouch as evaluated over time resident in the mouth of a test subject. The Y-axis depicts the total concentration of Cannabidiol remaining in the pouch and the X-axis depicts the amount of time resident in the mouth of a test subject.

Since the present experiments were essentially multiple experiments run in parallel, the variability of the curves in FIGS. 2 & 3 is partially explained, particularly with regard to the apparent "rise" in CBD concentrations remaining in the pouch in the prior pouch at the 5 minute and 30 minute time periods. While not intending to be bound by any specific theory of operation, this in fact was not a rise in that CBD did not return to the pouch after leaving it, but is rather an artifact of the separate use of multiple identically prepared pouches. Attempts were made to reduce variability by subject selection, timing mode, accuracy in pouch preparation, consistency in chromatography, storage and transport of used pouches, and other aspects.

Figure 4:
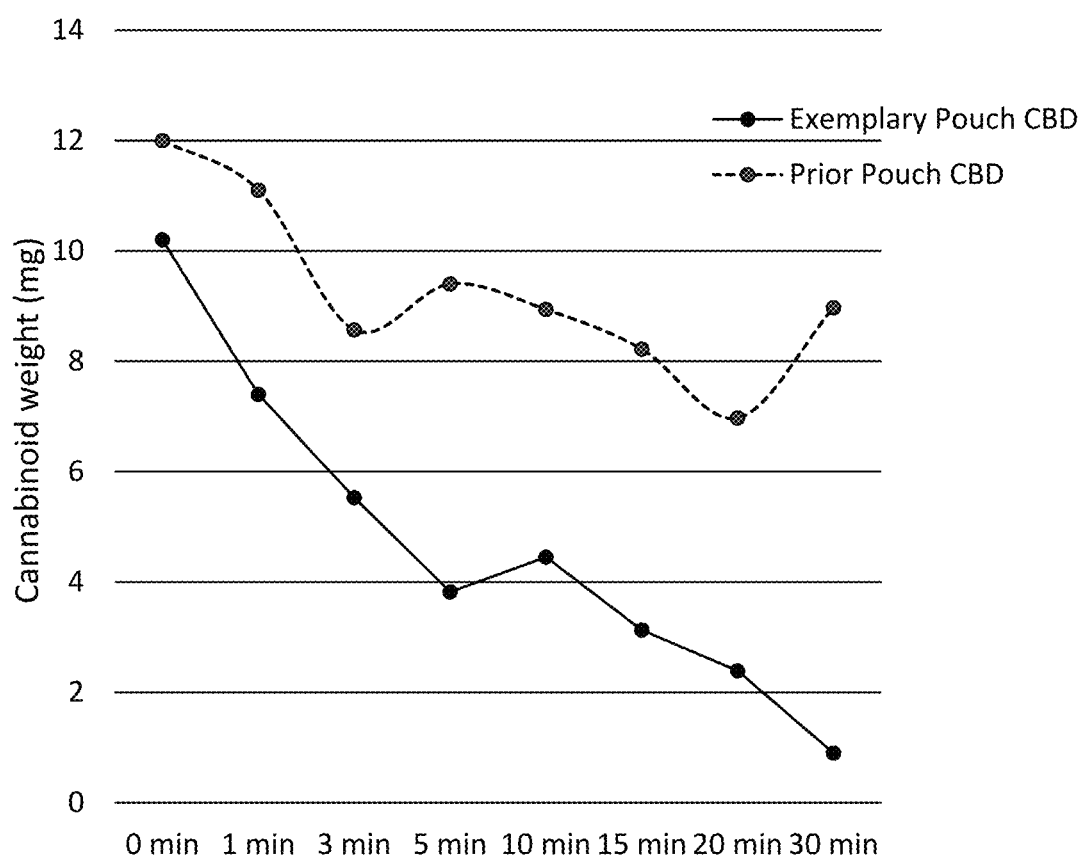
FIG. 4 depicts additional results showing the reduction of the cannabidiol in an exemplary pouch and a conventional pouch as evaluated over time resident in the mouth of a test subject. The Y-axis depicts the total concentration of Cannabidiol remaining in the pouch and the X-axis depicts the amount of time resident in the mouth of a test subject.

The results of liquid chromatography analysis of the pouches are set forth in FIGS. 3 and 4. In both FIGS. 3 and 4, the Y-axis depicts the total concentration of Cannabidiol remaining in the pouch and the X-axis depicts the amount of time resident in the mouth of a test subject.

These results indicate that cannabinoids are more rapidly released from a pouch formed from apertured fibrous matrix according to the present disclosure than a pouch formed from a standard fibrous matrix lacking apertures.

A similar experimental design is prepared and evaluated for a terpene as an active ingredient.

In one embodiment, the apertured fibrous matrix is configured such that a pouch formed from the apertured fibrous matrix has a release rate of a cannabinoid (e.g., CBD, tetrahydrocannabinol, etc.) that is at least 50% faster, when measured from 0 to 60 seconds compared to a pouch formed from a standard fibrous matrix lacking apertures, for example, a pouch formed from the apertured fibrous matrix has release rate that is at least 55%, 60%, 65%, 70%7, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195% or 200% faster than the release rate of a pouch formed from standard fibrous matrix lacking apertures when measured from 0 to 60 seconds. In certain embodiments, the release rate of a cannabinoid (e.g., CBD, tetrahydrocannabinol, etc.) over 1 minute to 30 minutes is between 3 to 5 times faster in a pouch formed of the apertured fibrous matrix compared to a pouch formed from a standard fibrous matrix lacking apertures.

While the release characteristics measured and noted herein are in connection with a cannabinoid, namely CBD, the same surprisingly increased release characteristics exist in connection with terpene and flavor. The flavor is perceived as more intense for the same fill composition used in a pouch formed of the apertured fibrous matrix versus in a pouch formed of a standard fibrous matrix lacking apertures. In certain embodiments, the release rate of a terpene or a composed flavor characteristic over 1 minute to 30 minutes is between 3 to 5 times faster in a pouch formed of the apertured fibrous matrix compared to a pouch formed from a standard fibrous matrix lacking apertures.

The results discussed above in connection with the apertured fibrous matrix comprised of viscose demonstrate that the size and concentration of the apertures substantially increase the release of cannabinoid constituents in comparison to standard fibrous matrix lacking apertures. The size of the apertures are also adapted to retain physical substrate in the pouch.

In one embodiment a pouch for administration of cannabidiol is provided, wherein a cannabidiol containing fill material comprises cannabidiol, one or more of coconut coir, kenaf, abaca, flax, hemp, jute, ramie, sisal, rice, bamboo, corn husk, silk husk, fruit skin, straw, soy, mint leaf, spearmint leaf, lettuce leaf, synthetic fibers, animal-derived fibers, chitin, and kudzu root, and optionally one or more of a natural oil, a sweetener, a stabilizer or a flavorant.

The above embodiments are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

Citation of the above publications or documents is not intended as an admission that any of the foregoing is pertinent prior art, nor does it constitute any admission as to the contents or date of these publications or documents.

I claim:

1. A pouch for administration of a cannabinoid, comprising a fibrous matrix material incorporating a plurality of apertures defining a sealed pouch, and a cannabinoid containing cured fill material positioned within the sealed pouch, wherein the cannabinoid containing cured fill material comprises a cannabinoid extract or oil, wherein the cannabinoid extract or cannabinoid oil is extracted from source material and consists essentially of cannabidiol, cannabinol, cannabigerol, cannabichromene, cannabidivarol, tetrahydrocannabidiol, tetrahydrocannabigerol, tetrahydrocannabichromene, tetrahydrocannabidivarol, $\Delta^8$-THC, or two or more of the foregoing, wherein the cannabinoid containing cured filled material comprises at least one of a flavorant, a sweetener, or a stabilizer, wherein the cured fill material is produced by a process comprising mixing and curing coconut coir together with the cannabinoid extract cannabinoid oil, palm oil and at least one of a flavorant, a sweetener, or a stabilizer for at least 24 hours prior to positioning the cured fill material in the pouch and sealing the pouch;

wherein at least 60% of the cannabinoid containing fill material is comprised of particles having a mean size range larger than the aperture size, wherein each of the plurality of apertures is defined by the an aperture size of between about 400 μm to about 800 μm in diameter, wherein a distance between apertures is from 1.5 millimeters to 9 millimeters.

2. The pouch for administration of a cannabinoid of claim 1, wherein the pouch is adapted to release between 40% to 90% of the cannabinoid present in the fill material in under 10 minutes when placed in a mouth of a user.

3. The pouch for administration of a cannabinoid of claim 1, wherein at least about 50% of the plurality of apertures have the identified size.

4. The pouch for administration of a cannabinoid of claim 1, wherein at least about 90% of the plurality of apertures have the identified size.

5. The pouch for administration of a cannabinoid of claim 1, wherein the each of the plurality of apertures is circular in shape.

6. The pouch for administration of a cannabinoid of claim 1, wherein the cannabinoid containing fill material further comprises a terpene and a natural oil.

7. The pouch for administration of a cannabinoid of claim 1, wherein the cannabinoid containing fill material comprises a cannabidiol isolate.

8. The pouch for administration of a cannabinoid of claim 1, wherein the plurality of apertures comprise holes extending through the fibrous matrix material.

9. The pouch for administration of a cannabinoid of claim 1, wherein the cannabinoid containing fill material comprises an electrospun nanofiber, wherein the cannabinboid is THC, and the THC is comprised in the electrospun nanofiber.

10. The pouch for administration of a cannabinoid of claim 1, wherein the cannabinoid containing fill material comprises a terpene selected from the group consisting of one or more of borneol, caryophyllene, cineole/eucalyptol, delta3carene, limonene, linolool, myrcene, pinene, pulegone, d-limonene linalool, 1,8-cineole (eucalyptol), terpineol-4-ol, p-cymene, and $\Delta$-3-carene.

11. The pouch for administration of a cannabinoid of claim 1, wherein the cannabinoid containing fill material comprises a blended composition having a total weight, and cannabinoid containing fill material includes the cannabinoid between about 5% to at or about 20% of the total weight.

12. The pouch for administration of a cannabinoid of claim 1, wherein the fibrous matrix material is selected from one or more of viscose, cellulose, polyester, cotton, hemp, cellulose acetate, polylactic acid, polypropylene, modal cellulose, and rayon.

13. A pouch for administration of a cannabinoid, comprising a fibrous matrix material incorporating a plurality of apertures defining a sealed pouch, and a cannabinoid ingredient containing cured fill material positioned within the sealed pouch and at least about 90% of the plurality of apertures is defined by an aperture size of between about 200 μm to about 1000 μm in diameter, wherein the plurality of apertures are present in the fibrous matrix material at an aperture density of between 1 to 100 per square centimeter;

the cannabinoid containing cured fill material comprises a cannabinoid and/or a terpene, wherein the cannabinoid consists of a cannabinoid extract or cannabinoid oil, wherein the cannabinoid extract or cannabinoid oil is extracted from the source material;

the fibrous matrix material selected from one or more of viscose, cellulose, polyester, cotton, hemp, cellulose acetate, polylactic acid, polypropylene, modal cellulose, rayon;

the cannabinoid containing cured fill material further comprises one or more of a natural oil, a sweetener, a stabilizer, or a flavorant;

wherein the cannabinoid containing cured filled material is composed of a mixture of the cannabinoid, coconut coir, palm oil, and the one or more of a natural oil, sweetener, a stabilizer, or a flavorant, and wherein the mixture is cured for at least 24 hours prior to positioning in and sealing the pouch;

where the pouch is adapted to release between 40% to 90% of the cannabinoid present in the fill material in between 5 to 10 minutes when placed in a mouth of a user; and wherein a distance between apertures is from 1.5 millimeters to 9 millimeters.

14. The pouch of claim 1, wherein the mixture is cured for between 24 hours to 72 hours prior to positioning in and sealing the pouch.

15. The pouch of claim 13, wherein the mixture is cured for between 24 hours to 72 hours prior to positioning in and sealing the pouch.

* * * * *